United States Patent
Suzuki (12)

(10) Patent No.: US 8,659,305 B2
(45) Date of Patent: Feb. 25, 2014

(54) DETECTION DEVICE FOR DETECTING IMPEDANCE OF SENSOR ELEMENT IN GAS SENSOR AND SENSOR UNIT EQUIPPED WITH DETECTION DEVICE

(75) Inventor: Toshiyuki Suzuki, Kiyosu (JP)

(73) Assignee: Denso Corporation, Kariya (JP)

( * ) Notice: Subject to any disclaimer, the term of this patent is extended or adjusted under 35 U.S.C. 154(b) by 255 days.

(21) Appl. No.: 13/108,091

(22) Filed: May 16, 2011

(65) Prior Publication Data

US 2011/0279129 A1    Nov. 17, 2011

(30) Foreign Application Priority Data

May 14, 2010    (JP) .................................. 2010-111814

(51) Int. Cl.
*G01R 27/04*    (2006.01)
*G01R 27/00*    (2006.01)
*G01R 27/08*    (2006.01)

(52) U.S. Cl.
USPC .......................... 324/647; 324/600; 324/705

(58) Field of Classification Search
USPC ......... 324/649, 654, 717, 122, 464, 465, 525,
324/600, 605, 606, 616, 634–635, 642–643,
324/647, 656, 658, 672, 671, 691, 693–694,
324/705; 204/406, 425, 427; 307/307, 350,
307/351, 359
See application file for complete search history.

(56) References Cited

U.S. PATENT DOCUMENTS

| | | | | |
|---|---|---|---|---|
| 5,001,726 A | * | 3/1991 | Kawai et al. ................... | 375/317 |
| 5,025,176 A | * | 6/1991 | Takeno ............................ | 327/58 |
| 6,120,663 A | * | 9/2000 | Kato et al. ..................... | 204/401 |
| 6,478,940 B1 | * | 11/2002 | Suzuki et al. ................. | 204/425 |
| 6,480,311 B1 | * | 11/2002 | Okuda et al. .................. | 398/135 |
| 6,789,224 B2 | * | 9/2004 | Miura ............................ | 714/744 |
| 7,940,072 B2 | * | 5/2011 | Suda ........................ | 324/762.01 |
| 8,278,961 B2 | * | 10/2012 | Watanabe et al. ......... | 324/762.01 |
| 8,310,248 B2 | * | 11/2012 | Gotoh et al. .................. | 324/686 |

(Continued)

FOREIGN PATENT DOCUMENTS

| | | |
|---|---|---|
| JP | P2004-516453 A | 6/2004 |
| JP | 2005-274554 | 10/2005 |

(Continued)

OTHER PUBLICATIONS

Japanese Office Action dated Apr. 24, 2012, issued in corresponding Japanese Application No. 2010-111814 with English translation.

*Primary Examiner* — Joshua Benitez-Rosario
(74) *Attorney, Agent, or Firm* — Nixon & Vanderhye PC (57) ABSTRACT

In a sensor control circuit, an impedance signal output unit has a HPF, a P/H circuit, a LPF, etc., and detects an element impedance of a sensor element on the basis of an impedance response signal which is alternately changed in response to an alternating current signal supplied to the sensor element. The P/H circuit has an input comparator which inputs an impedance detection voltage Vz after the HPF, a rectifying element connected to the P/H circuit, and a hold capacitor which is charged by the output of the input comparator. The input comparator has a constant current circuit and a transistor. The constant current circuit limits an updating value of a hold voltage value Vph of the hold capacitor every alternating current period. The sensor control device detects the element impedance of the sensor element with high accuracy while preventing influence of noise.

8 Claims, 6 Drawing Sheets

(56) References Cited

U.S. PATENT DOCUMENTS

| | | |
|---|---|---|
| 8,358,142 B2 * | 1/2013 | Maharyta ............... 324/658 |
| 2003/0127323 A1 | 7/2003 | Bolz |
| 2004/0089545 A1 * | 5/2004 | Kawase et al. ............ 204/425 |
| 2005/0161325 A1 | 7/2005 | Inoue et al. |
| 2007/0018637 A1 * | 1/2007 | Kim et al. ............... 324/158.1 |
| 2008/0094079 A1 * | 4/2008 | Suzuki et al. ............ 324/713 |
| 2009/0072866 A1 * | 3/2009 | Walker ................... 327/62 |
| 2009/0322379 A1 * | 12/2009 | Tomita .................... 327/58 |

FOREIGN PATENT DOCUMENTS

| | | |
|---|---|---|
| JP | 2006-105959 | 4/2006 |
| JP | 2006-343306 | 12/2006 |
| JP | 2006-343317 | 12/2006 |
| JP | 2008-304383 | 12/2008 |
| JP | 2010-071898 | 4/2010 |

* cited by examiner

SUPPLIED VOLTAGE

FIG.8B

ELEMENT CURRENT

FIG.8C

RESET    HOLD VOLTAGE VALUE

P/H OUTPUT

FIG.8D

ON
OFF
HEAT UNIT

FIG.8E

NOISE

ELEMENT CURRENT (WITH NOISE)

FIG.8F

ERROR

P/H OUTPUT (WITH NOISE)

DETECTION DEVICE FOR DETECTING IMPEDANCE OF SENSOR ELEMENT IN GAS SENSOR AND SENSOR UNIT EQUIPPED WITH DETECTION DEVICE

CROSS-REFERENCE TO RELATED APPLICATION

This application is related to and claims priority from Japanese Patent Application No. 2010-111814 filed on May 14, 2010, the contents of which are hereby incorporated by reference.

BACKGROUND OF THE INVENTION

1. Field of the Invention

The present invention relates to a detection device for detecting an element impedance of a sensor element capable of detecting a concentration of oxygen contained in target detection gas such as exhaust gas emitted from an internal combustion engine, and also relates to a sensor unit equipped with the detection device.

2. Description of the Related Art

There have been proposed various conventional techniques for detecting an element impedance of a sensor element assembled in a gas sensor such as an air/fuel sensor (A/F sensor) on the basis of detection results of a current change value and a voltage change value when a supplied voltage or current is temporarily and/or continuously changed. Such an A/F sensor has a sensor element made of solid electrolyte.

The presence of noise which is overlapped or superimposed on an impedance detection signal output from the sensor element in the gas sensor decreases the detection accuracy of the sensor element. Various conventional techniques have been proposed so as to eliminate noise components from an impedance detection signal. There are various types of noise which affect such an impedance detection signal, for example, heater noise generated when one or more heater parts are turned on and off in order to activate the sensor element, and ignition noise generated when an internal combustion engine is ignited.

A description will be given of the occurrence of incorrect detection caused when an element impedance of a sensor element in a gas sensor is detected with reference to FIG. 8A to FIG. 8F.

FIG. 8A to FIG. 8F are timing charts showing waveforms of various signals when an element impedance of a sensor element is detected during a predetermined period of time.

Figure 8A:
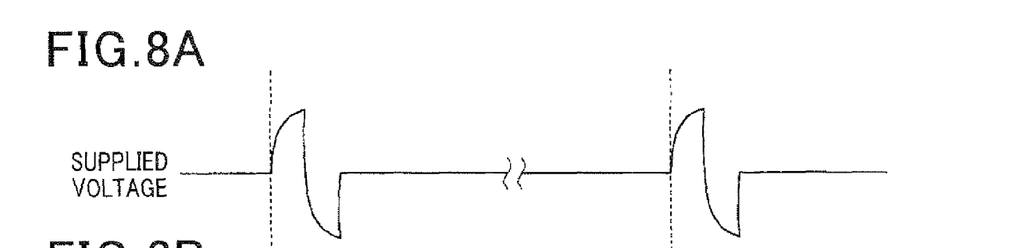
FIG. 8A is a timing chart showing a waveform of an alternating current (AC) voltage which is temporarily supplied to the sensor element during a predetermined period of time when an element impedance of the sensor element is detected.
Figures 8B, 8C, 8D:
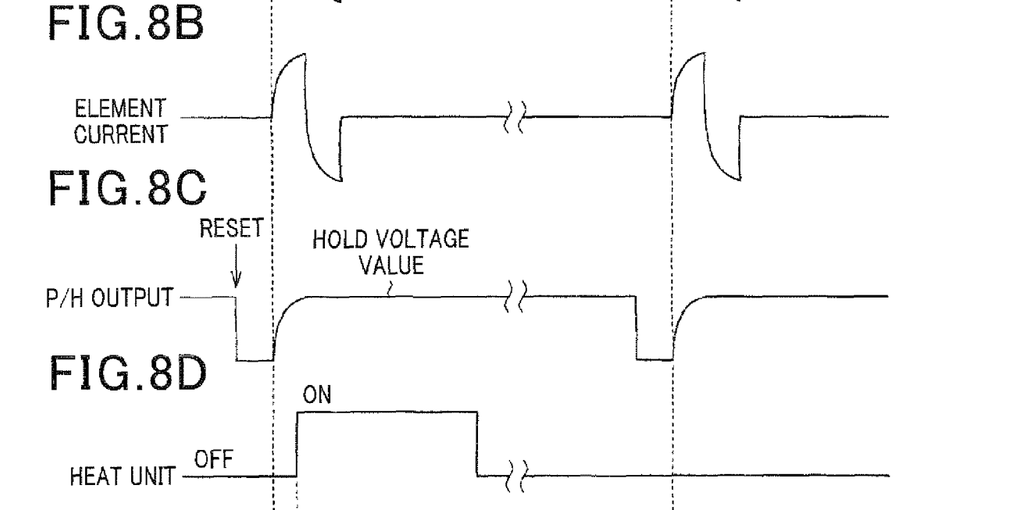
FIG. 8B is a timing chart showing a change of the element current which flows in the sensor element when the sensor element is detected shown in FIG. 8A.
FIG. 8C is a timing chart showing a peak hold value of a peak hold circuit.
FIG. 8D is a timing chart showing the turning on and off of heater parts by supplying electric power to the heater parts.

In particular, FIG. 8A is a timing chart showing a waveform of an alternating-current (AC) voltage which is temporarily supplied to the sensor element during a predetermined period of time when an element impedance of the sensor element is detected. FIG. 8B is a timing chart showing a change of the element current which flows in the sensor element when the sensor element is detected shown in FIG. 8A.

FIG. 8C is a timing chart showing a peak hold value of a peak hold circuit.

A detection device calculates the element impedance of the sensor element in the gas sensor on the basis of the peak hold value which is held in the peak hold circuit.

Because a control device (not shown) executes a duty control for repeatedly turning on and off the heater parts formed in the gas sensor, there is a possibility of the timing of detecting the element impedance agreeing with the timing of turning on and off the heater parts.

FIG. 8D is a timing chart showing the turning on and off of heater parts by supplying electric power to the heater parts.

Figure 8E:
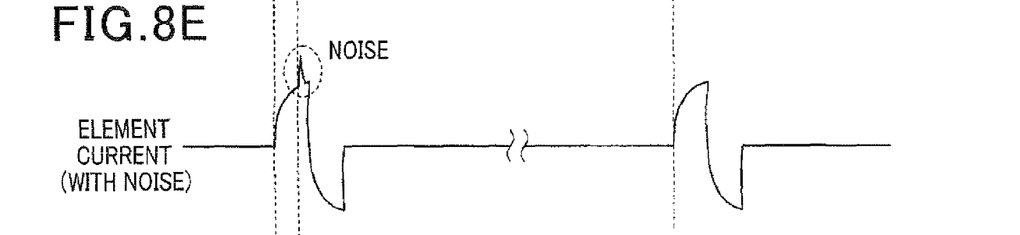
Figure 8F:
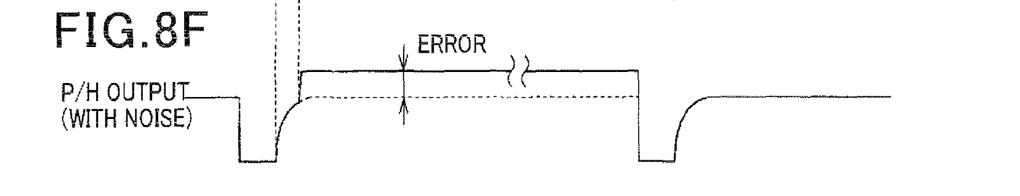
FIG. 8F is a timing chart showing an error of a peak hold (P/H) value with noise

FIG. 8E is a timing chart showing an element current with heater noise generated by turning on and off of the heater parts. FIG. 8F is a timing chart showing an error of a peak hold (P/H) value with noise.

As shown in FIG. 5D, when the heater parts in the gas sensor are turned on, namely, electric power is supplied to the heater parts, heater noise is generated and superimposed on an element current. This element current flows in the sensor element in the gas sensor, and supplied to the control device. In this case, as shown in FIG. 8F, the peak hold circuit holds the peak hold value with an error which is different from its true P/H value. As a result, the control device calculates an element impedance of the sensor element with error.

For example, Japanese patent laid open publication No. JP 2006-343317 discloses a configuration of a conventional technique in which a filter means (a low pass filter) is placed at a front stage of a hold circuit in order to eliminate noise from a detection signal regarding an element impedance of a sensor element. The hold circuit holds a voltage changed value when an element impedance of a sensor element is detected. This conventional technique can eliminate noise which is superimposed on the detection signal regarding an element impedance of a sensor element at a stage before the voltage hold circuit holds a voltage changed value in addition to noise which is superimposed on the detection signal of the element impedance. This makes it possible to prevent the accuracy of detecting the element impedance of the sensor element from being decreased, where the decrease of the detection accuracy is caused by incorrect detection of the voltage hold value caused when the voltage hold circuit holds the voltage change value.

However, in the filter means placed at a front stage of the voltage hold circuit in the configuration disclosed in JP 2006-343317, the filter means eliminates a changed response value of an element current in addition to noise. This shifts the voltage change value held in the voltage hold circuit from its true value. Accordingly, it is difficult for the conventional configuration disclosed in JP 2006-343317 to correctly and adequately eliminate noise while maintaining the voltage changed value.

Still further, in order to avoid incorrect detection of the element impedance of a sensor element of a gas sensor caused by heater noise, it is effective for the timing of detecting the element impedance of the sensor element to be shifted from the timing of turning on and off the heater parts. However, this technique is required to have: (a) a sensor control circuit (sensor control IC circuit); and (b) the function of calculating an impedance value of the sensor element on the basis of an output signal of the sensor control circuit, and the function of executing the timing control between the sensor control circuit and a microcomputer capable of controlling the timing to supply electric power to the heater parts. The control device is required to have a complicated configuration and operation in order to execute these functions.

SUMMARY OF THE INVENTION

It is an object of the present invention to provide a detection device for detecting the element impedance of a sensor element in a gas sensor with high accuracy while effectively eliminating external noise.

To achieve the above purposes, the present invention provides a detection device which detects an element impedance of a sensor element. The sensor element is comprised of a solid electrolyte. The detection device is comprises of an alternating current signal supplying means and an impedance detection means. The alternating current signal supplying means supplies an alternating current signal to a sensor element. The impedance detection means detects an element impedance of the sensor element on the basis of one of a current and a voltage of an impedance response signal which is alternately changed in response to the alternating current signal supplied to the sensor element. In particular, the impedance detection means is comprised of a hold means and a limit means. The hold means holds a hold value and updates the hold value when receiving the impedance response signal every an alternating current period of the impedance response signal. The limit means limits an updated value of a hold value of the hold means every alternating current period of the impedance response signal.

In the configuration of the detection device, the hold value of the hold means is sequentially updated in accordance with the impedance response signal. This impedance response signal is alternately changed in response to the alternating current signal which is supplied to the sensor element when the element impedance of the sensor element is detected. The detection device detects the element impedance of the sensor element on the basis of the hold value of the hold means. For example, the hold means is a hold capacitor.

Because the hold value of the hold means is updated while limiting the updating value every alternating current period, even if noise is superimposed on the impedance response signal, it is possible to limit the change value of the hold value caused by the noise. This makes it possible to suppress decreasing of the detection accuracy of the detection device caused by noise, where the detection device detects the element impedance of the sensor element. Further, the hold value of the hold means is repeatedly updated every alternating current period while the alternating current signal is supplied to the sensor element. After the hold value of the hold means reaches its peak value, the hold means (such as the hold capacitor) maintains the peak value.

In addition, in a configuration in which the sensor element has the heater parts embedded therein and the heater parts are turned on and off in order to activate the sensor element, it is possible for a microcomputer such as a CPU to execute a process of controlling the timing of detecting the element impedance and the timing when electric power is supplied to the heater parts in order to eliminate heater noise caused when the heater parts are turned on and off. As a result, it is possible for the detection device according to the present invention to have a high accuracy of detecting the element impedance of the sensor element while avoiding influence caused by the above noise.

In the detection device as another aspect of the present invention, the impedance detection means is comprised of an input comparator and a hold capacitor. The input comparator is placed before the hold means, namely, at a front position of the hold means on a way of an electrical path on which the impedance response signal is transferred, and compares the impedance response signal with the current hold value of the hold means. The hold capacitor serves as the hold means which updates the hold value by being charged on the basis of the comparison result of the input comparator. In the detection device according to the present invention, the limit means limits the output of the input comparator in order to limit the updating value of the hold value every alternating current period.

According to the detection device of the present invention having the above configuration, because the output of the input comparator is limited, the updating value of the hold value in the hold means (hold capacitor) is limited every alternating current period. In this case, although the noise is not eliminated from the input signal of the input comparator, it is possible to eliminate influence of the noise from the output of the input comparator. Accordingly, this makes it possible to efficiently eliminate the noise from the impedance response signal.

In the detection device as another aspect of the present invention, the input comparator is comprised of a constant current circuit. The constant current circuit supplies a constant current when the hold capacitor is charged. In particular, an updating speed of the hold value in the hold means is determined by the magnitude of the constant current supplied from the constant current circuit, and the output of the input comparator is limited by the updating speed.

According to the detection device of the present invention having the above configuration, the hold value (charged voltage) of the hold means is sequentially charged by the constant current supplied from the constant current circuit. In this case, the updating speed (updating value every alternating current period) of the hold value is determined by the magnitude of the constant current supplied from the constant current circuit. That is, the more the magnitude of the constant current is decreased, the more the updating speed of the hold value is decreased, but this increases the noise resistance function of the detection device according to the present invention. It is possible for the control device according to the present invention to easily adjust the updating speed of the hold value of the hold capacitor by adjusting the magnitude of the constant current supplied from the constant current circuit.

In the detection device as another aspect of the present invention, the impedance detection means comprises discharge means which discharges the hold capacitor at a discharging speed which is lower than the charging speed of the constant current.

This configuration of the detection device makes it possible to return the hold value to its correct value after the noise is superimposed on the impedance response signal. In addition, even if the element impedance value of the sensor element is changed according to the temperature change of the sensor element, it is possible for the control device according to the present invention to update the hold value of the hold capacitor (hold means) increasing and decreasing.

It is not always necessary to reset the hold value of the hold capacitor. In the detection device as another aspect of the present invention, the impedance detection means is comprised of a reset means. The reset means resets the hold value of the hold means. The impedance detection means inhibits the detection of the element impedance of the sensor element during a period after the reset of the hold value of the hold means.

It is possible to connect the detection device according to the present invention with a gas sensor in order to make a sensor unit. This application makes it possible to provide the sensor unit with an improved and enhanced detection accuracy of the element impedance of a sensor element while eliminating influence of noise.

BRIEF DESCRIPTION OF THE DRAWINGS

A preferred, non-limiting embodiment of the present invention will be described by way of example with reference to the accompanying drawings, in which:

FIG. 5E is a timing chart showing an element current with heater noise generated by turning on and off of the heater parts.

DETAILED DESCRIPTION OF THE PREFERRED EMBODIMENTS

Hereinafter, various embodiments of the present invention will be described with reference to the accompanying drawings. In the following description of the various embodiments, like reference characters or numerals designate like or equivalent component parts throughout the several diagrams.

Embodiment

A description will be given of a sensor control device as a detection device for detecting an element impedance of a sensor element in a gas sensor according to an embodiment of the present invention with reference to FIG. 1 to FIG. 7.

Figure 1:
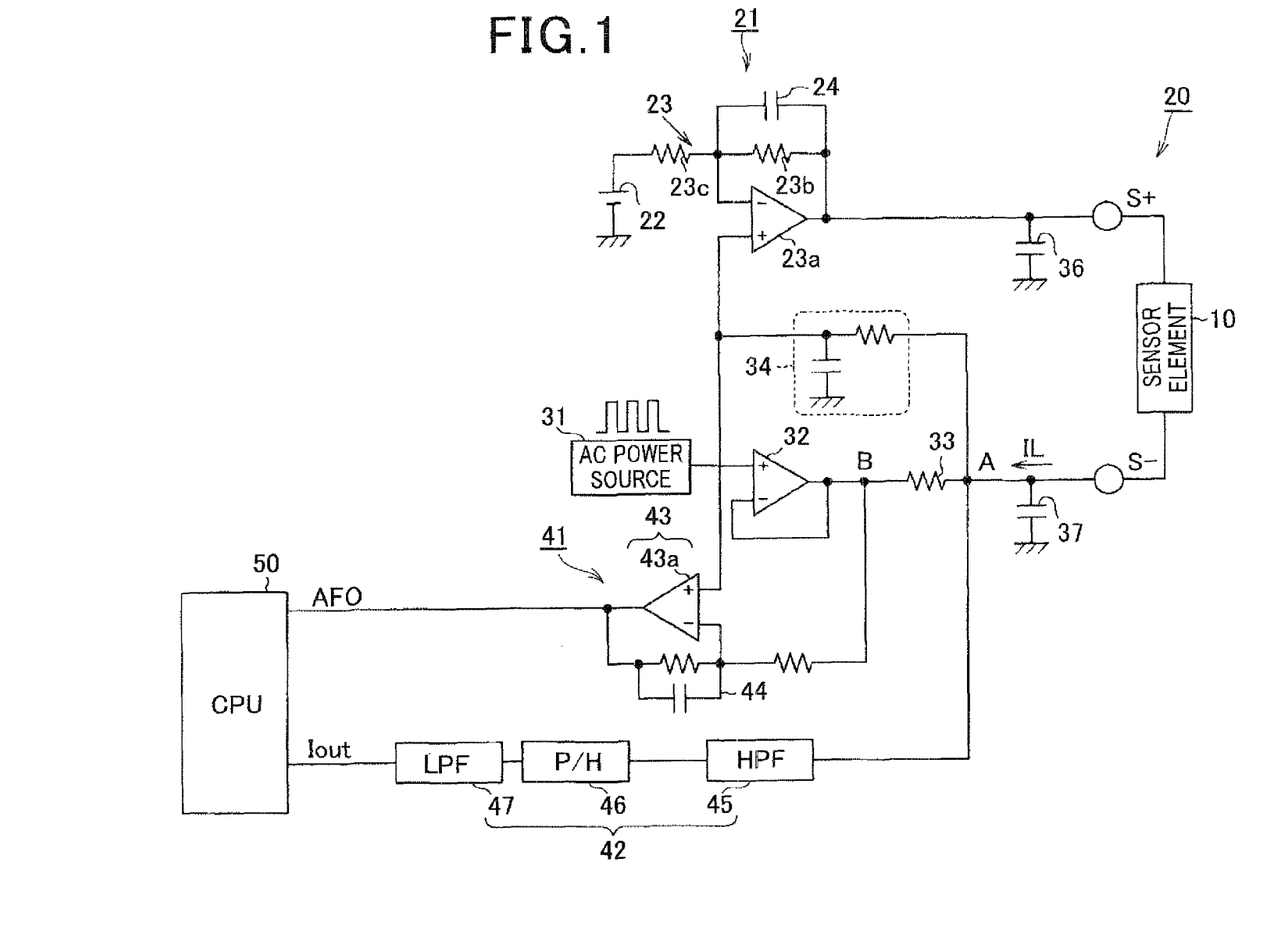
FIG. 1 is a view showing a circuit configuration of a sensor control device as a detection device for detecting an element impedance of a sensor element in a gas sensor according to an embodiment of the present invention.

FIG. 1 is a view showing a circuit configuration of a sensor control device 20 as the detection device according to the embodiment of the present invention. The sensor detection device 20 detects the element impedance of a sensor element of a gas sensor such as an A/F sensor.

The sensor control device 20 according to the embodiment is supplied to an air/fuel (A/F) detection device equipped with such an A/F sensor. The A/F sensor detects a concentration of oxygen (as air/fuel ratio (A/F ratio)) contained in exhaust gas as target detection gas emitted from an on-vehicle engine. An ECU (engine control unit) in an A/F control system receives a detection signal regarding the detection result of the A/F detection device. The A/F control system executes a stoichiometry A/F control, and lean burn A/F control. In the stoichiometry A/F control, the A/F control system executes a feedback control of A/F ratio near the stoichiometry. In the lean burn control, the A/F control system executes a feedback control of A/F ratio within a predetermined lean area.

A description will now be given of a structure of the sensor element 10 in the A/F sensor with reference to FIG. 2.

Figure 2:
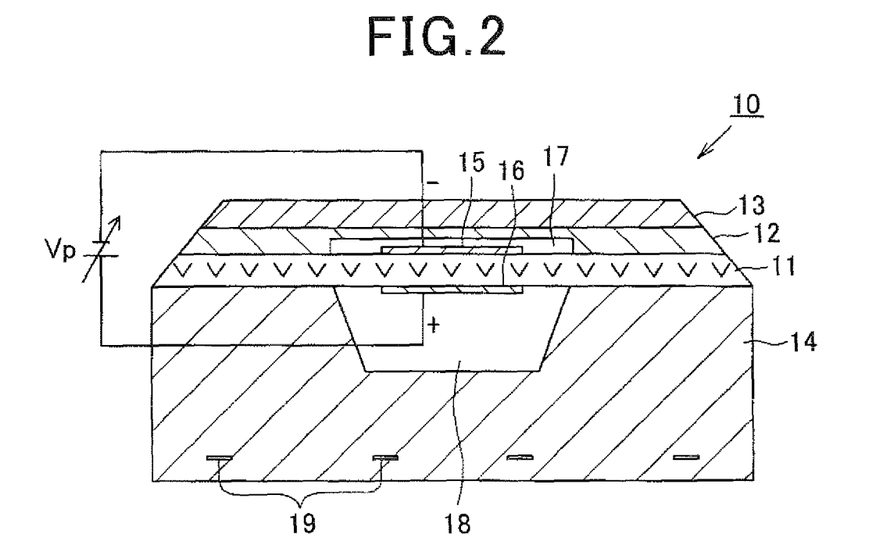
FIG. 2 is a view showing a cross section of a lamination structure of a sensor element in an A/F sensor.

FIG. 2 is a view showing a cross section of a lamination structure of the A/F sensor equipped with the sensor element 10.

In general, the A/F sensor is equipped with the sensor element 10. The sensor element 10 is composed of a solid electrolyte. When receiving a predetermined supplying voltage, the sensor element 10 outputs an element current which corresponds to a concentration of oxygen contained in exhaust gas as a target detection gas emitted from a diesel engine.

The sensor element 10 has a longitudinal structure extending in a direction which is at right angles to the surface of FIG. 2. The sensor element 10 is covered with a housing case or an element cover. That is, the housing case in the A/F sensor accommodates the sensor element 10.

The sensor element 10 is comprised of a solid electrolyte layer 11, a diffusion resistance layer 12, a shield layer 13 and an insulation layer 14. As shown in FIG. 2, the solid electrolyte layer 11, the diffusion resistance layer 12, the shield layer 13 and the insulation layer 14 are stacked in vertical direction in order to make a lamination or stack structure. The lamination is covered with a protection layer (not shown).

The solid electrolyte layer 11 having a rectangle plate shape is a sheet made of partially stabilized zirconia. The solid electrolyte layer 11 is placed or sandwiched between a pair of electrodes 15 and 16. That is, as shown in FIG. 2, the electrodes 15 and 16 face to each other through the solid electrolyte layer 11.

The diffusion resistance layer 12 is made of a porous sheet through which exhaust gas as a target detection gas is introduced into the electrode 15. The shield layer 13 is made of a compact layer which is capable of preventing the exhaust gas from being transmitted. The diffusion resistance layer 12 has a mixing chamber 17 which surrounds the electrode 15.

The diffusion resistance layer 12 and the shield layer 13 are made of ceramics composed of alumina, spinel, zirconia, etc. and produced by using a sheet forming method. Each of the diffusion resistance layer 12 and the shield layer 13 has a gas permeability which is changeable according to an average pore diameter and a porosity of ceramics.

The insulation layer 14 is made of high heat conductive ceramics such as alumina and has an atmosphere duct 18. The atmosphere duct 18 faces the electrode 16. A plurality of heater parts 19 is embedded in the insulation layer 14. When receiving electric power from a battery (not shown), the heater parts 19 made of a linear shaped heating body generate heat energy in order to heat the entire of the sensor element 10.

Ambient exhaust gas is introduced into the inside of the sensor element 10 having the above structure through a side part of the diffusion resistance layer 12, and passed through the diffusion resistance layer 12 in order to be introduced into the mixing chamber 17. The introduced exhaust gas finally reaches the electrode 15 in the sensor element 10. When the ambient exhaust gas has a lean A/F ratio, oxygen contained in the exhaust gas is discomposed at the electrode 15, and then exhausted into the atmosphere duct 18 through the electrode 16.

On the other hand, when the exhaust gas has a rich A/F ratio, oxygen contained in the atmosphere duct 18 is decomposed at the electrode 16, and then exhausted through the electrode 15.

Figure 3:
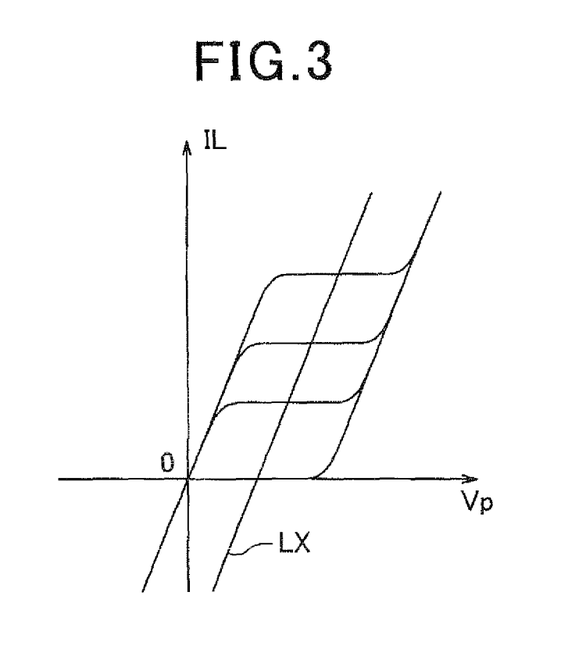
FIG. 3 is a view showing a V-I characteristics of the sensor element shown in FIG. 2.

FIG. 3 is a view showing an output characteristics (as a V-I characteristics) of the sensor element 10 shown in FIG. 2. In FIG. 3, the horizontal axis indicates a supplied voltage Vp.

The supplied voltage Vp shows a voltage difference between a positive terminal S+ and a negative terminal S− of the sensor element 10. The vertical axis indicates an element current IL.

In the V-I characteristics line shown in FIG. 3, the flat part, which is in parallel to the horizontal axis Vp, indicates a limiting current zone. The limiting current zone specifies the element current IL as a limiting current. The increase/decrease of the flat part corresponds to the increase/decrease of the A/F ratio of a fuel mixture. That is, the more the A/F ratio of the fuel mixture is shifted to a lean mixture side, the more the element current IL is increased.

On the other hand, the less the A/F ratio of the fuel mixture is shifted to a rich mixture side, the more the element current IL is decreased. The straight line indicates a supplied voltage characteristic line LX which is used for determining the supplied voltage Vp which is supplied to the sensor element 10. The slope of the supplied voltage characteristic line LX corresponds to a slope caused by a resistance. That is, the slope of the supplied voltage characteristic line LX is a slope which is shifted to a low voltage zone which is lower than a voltage of the limiting current zone.

Next, a description will now be given of the configuration of the sensor control circuit 20 as the detection device for detecting the element impedance of the sensor element 10 according to the embodiment with reference to FIG. 1.

As shown in FIG. 1, the sensor control circuit 20 has a supplying voltage control circuit 21. The supplying voltage control circuit 21 adjusts the voltage supplied to the positive terminal S+ of the sensor element 10 according to the magnitude of the element current IL. That is, the voltage supplied from the supplying voltage control circuit 21 is the terminal voltage VS+ at the positive terminal S+ which is connected to the electrode 16 in the sensor element 10.

The supplying voltage control circuit 21 is comprised of a reference power source 22 and an amplification circuit 23. The amplification circuit 23 is connected to the reference power source 22.

For example, the reference power source 22 supplies a voltage of 2.6 volts. The amplification circuit 23 is a non-inversion amplification circuit having a feedback resistance 23b and an input resistance 23c. The feedback resistance 23b and the input resistance 23c are connected to an inverse input terminal S− of an operational amplifier 23a. In the amplification circuit 23, a capacitor 24 is connected in parallel to the feedback resistance 23b.

In the configuration of the sensor control circuit 20, a low pass filter (LPF) is placed on a feedback path of the amplification circuit 23. The LPF prevents an oscillation of the supplied voltage. For example, the LPF has a cut-off frequency of 2.7 Hz.

A changeable voltage corresponding to the element current IL is supplied to the non-inverse input terminal (+terminal) of the operational amplifier 23a. The output terminal of the operational amplifier 23a is connected to the positive terminal (S+) of the sensor element 10.

The other terminal (as the negative terminal S− connected to the power source) of the sensor element 10 is connected in series to shunt resistance 33, a buffer 32, and an AC power source circuit 31. The AC power source circuit 31 serves as an alternating current voltage generation means for generating an AC voltage of approximately 10 to 20 kHz. The AC power source circuit 31 is comprised of an AC voltage generation circuit (not shown) and a low pass filter (LPF, not shown) for filtering the AC voltage supplied form the AC voltage generation circuit.

The AC power source circuit 31 generates the AC voltage which is changed within a predetermined voltage range around a predetermined reference voltage (for example, 2.2 volts in the embodiment). The AC voltage generated by the AC power source circuit 31 is supplied to the terminal S− of the sensor element 10. In the view of detecting an element impedance of the sensor element 10, it is sufficient for the AC voltage to have a frequency of not less than 3 kHz.

The shunt resistance 33 is used for detecting the element current IL. The shunt resistance 33 is a voltage conversion element which converts the element current IL to a voltage. That is, the shunt resistance 33 is placed on a current path between the AC power source circuit 31 and the sensor element 10. Through the current path the element current IL flows.

The voltage at the terminal of the shunt resistance 33, which is opposite to the sensor element 10 side, is a reference voltage (as the central voltage of the AC voltage of the AC power source circuit 31). The element current IL is detected at a connection node A between the shunt resistance 33 and the terminal S− of the sensor element 10.

The connection node A between the shunt resistance 33 and the sensor element 10 is further connected to the LPF 34. The LPF 34 is composed of a resistance and a capacitor. The LPF 34 is connected to the non-inverse input terminal (+ input terminal) of the operational amplifier 23a in the supplying voltage control circuit 21.

In the configuration shown in FIG. 1, an intermediate voltage (namely, a divided voltage obtained by the shunt resistance 33 and the sensor element 10) is supplied to the input terminal of the amplification circuit 23 in the supplying voltage control circuit 21. For example, the LPF 34 has a cut-off frequency 2 fc of 150 Hz.

The supplying voltage control circuit 21 and the AC power source circuit 31 correspond to the voltage supplying means. The voltage supplying means supplies the voltage to the positive terminal S+ and the negative terminal S− of the sensor element 10, respectively.

In the view of detecting the A/F ratio of a fuel mixture, the AC power source circuit 31 sets and supplies a reference voltage (which indicates a centre of the amplitude of a supplying voltage) to the terminal S− of the sensor element 10. The supplying voltage control circuit 21 sets and supplies a variable voltage, which corresponds to the element current IL, as the supplying voltage to be supplied to the terminal S+ of the sensor element 10.

The AC power source circuit 31 is an AC signal supplying means for supplying an AC voltage (AC signal) in order to detect an element impedance of the sensor element 10. In the embodiment, the AC power source circuit 31 generates the AC voltage having a centre voltage of 2.2 volts within an amplitude range of ±1.0 volts. Capacitors 36 and 37 are placed between the positive terminal S+ and the negative terminal S− of the sensor element 10 in order to eliminate noise, etc.

On the other hand, a pair of signal output parts is placed at a connection node A between the shunt resistance 33 and the terminal S− of the sensor element 10. The signal output parts are the A/F signal output part 41 and the impedance signal output part 42.

Each of the A/F signal output part 41 and the impedance signal output part 42 inputs the voltage at the connection node A which is a divided voltage obtained by the shunt resistance 33 and the sensor element 10.

The A/F signal output part 41 outputs an A/F detection signal AFO to the CPU 50. The signal output part 42 outputs an impedance detection signal Iout to the CPU 50.

The A/F signal output part 41 has a signal amplification function for amplifying the A/F detection signal AFO and an AC component eliminating function (or a function for extracting a direct current component from the AF detection signal AFO). The A/F signal output part 41 is comprised of an operational amplifier 43a, an amplification circuit 43 and a LPF 44.

In the embodiment, the LPF 44 is placed on a feedback path of the amplification circuit 43. The LPF 44 eliminates the AC component from the A/F detection signal.

The voltage at the terminal A and the voltage at the terminal B of the shunt resistance 33 is supplied to the input terminal of the operational amplifier 43a in the amplification circuit 41 in the A/F signal output part 41. In more detail, the voltage at the terminal A of the shunt resistance 33 is supplied to the non-inverse input terminal (+) of the operational amplifier 43a through the LPF 34, and the voltage at the terminal B of the shunt resistance 33 is supplied to the inverse input terminal (−) of the operational amplifier 43a.

In the configuration of the embodiment, the AC component of the voltage at the terminal A of the shunt resistance 33 is eliminated by the LPF 34, and the AC component of the voltage at the terminal B of the shunt resistance 33 is eliminated by the LPF 44. In the embodiment, the LPF 34 placed in the supplied voltage feedback path is also used for eliminating AC component in the A/F signal.

The impedance signal output part 42 is comprised of a high pass filter (HPF) 45, a peak hold circuit (P/H circuit) 46 and a low pass filter (LPF) 47. The impedance signal output part 42 has a function of amplifying the impedance detection signal Iout and a function of storing a peak value of the impedance detection signal Iout.

The HPF 45 eliminates a direct current component (corresponding to the direct current component of the A/F signal) contained in the voltage at the terminal A of the shunt resistance 33 from the A/F signal. After this, the P/H circuit 46 holds the peak voltage of the output signal of the HPF 45. Further, the LPF 47 eliminate a high frequency component of the output signal of the P/H circuit 46, and The LPH 47 outputs the impedance detection signal Iout to the CPU 50.

The CPU 50 which acts as a control means. The CPU 50 receives the A/F detection signal AFO supplied from the A/F signal output part 41 and the impedance detection signal Iout supplied from the impedance signal output part 42. The CPU 50 is a known arithmetic device equipped with an arithmetic part and a memory part (various memories such as a read only memory (ROM) and a random access memory (RAM)). An analogue to digital (A/D) conversion unit inputs the A/F detection signal AFO and the impedance detection signal Tout.

The CPU 50 calculates an A/F (concentration of oxygen) of a target detection gas on the basis of the A/F detection signal AFO, and calculates an element impedance Rac of the sensor element 10 on the basis of the impedance detection signal Iout.

Each of the A/F signal output part 41 and the impedance signal output part 42 amplifies a voltage signal with a respective amplification rate. The amplification rate in each of the A/F signal output part 41 and the impedance signal output part 42 is determined on the basis of a voltage level of each of the A/F detection signal component and the impedance detection signal component, and a voltage processing range (of 0 to 5 volts) of the AD conversion unit in the CPU 50. In the embodiment, the amplification rate of the A/F signal output part 41 is within a range of 10 to 20 times, and the amplification rate of the impedance signal output part 42 is a value of five times.

In the above configuration of the sensor control device according to the embodiment, when the AC power source circuit 31 supplies the AC voltage to the sensor element 10, the element current flows in the sensor element 10. The element current is a sum of a current component corresponding to an A/F (as a concentration of oxygen in exhaust gas as a target detection gas) and a current component corresponding to the element impedance.

The voltage at the connection node A between the shunt resistance 33 and the sensor element 10 has the amplitude which is changed according to the period of the sensor supplying voltage (according to the frequency of the AC voltage). This connection node A is a detection point at which the A/F detection signal (AFO) and the impedance detection signal (Iout) are detected. The A/F signal output part 41 and the LPF 34 extract a current component (a direct current component) corresponding to the A/F ratio at each time from the element current on the basis of the voltage at the connection node between the shunt resistance 33 and the sensor element 10. The A/F signal output part 41 amplifies the extracted current component by a predetermined amplification rate and outputs the amplified component as the A/F detection signal AFO to the CPU 50.

The impedance signal output part 42 extracts a current component (as an AC component) corresponding to the element impedance at each time from the voltage at the connection node between the shunt resistance 33 and the sensor element 10. The impedance signal output part 42 detects and outputs a peak value of the extracted current component as the impedance detection signal Iout to the CPU 50.

The impedance signal output part 42 detects a response current which is alternately changed in response to the AC voltage supplied to the sensor element 10.

The CPU 50 calculates the A/F value (as a concentration of exhaust gas) on the basis of the A/F detection signal AFO, and calculates the element impedance Rac of the sensor element 10 on the basis of the impedance detection signal Iout.

The CPU 50 has a heater control function which controls the operation of the heater parts 19 of the sensor element 10. That is, the CPU 50 calculates the element impedance Rac of the sensor element 10 at a predetermined period of time on the basis of the impedance detection signal Iout, and executes a feedback control of adjusting the electric power to be supplied to the heater parts 19 embedded in the sensor element 10 so that the calculated element impedance Rac becomes equal to a target impedance value. For example, the CPU 50 executes a pulse width modulation control (PWM control). This PWM control makes it possible to maintain the optimum activation state of the sensor element 10.

Although the A/F detection signal component and the impedance detection signal component, which are detected at the connection node A between the shunt resistance 33 and the sensor element 10, have a different voltage level, the A/F signal output part 41 and the impedance signal output part 42 input these components through a different signal path, and amplify these components, respectively, this makes it possible to suppress decreasing or deteriorating of the detection accuracy caused by a difference of the voltage level. For example, when these signal components are amplified on the basis of the A/F detection signal component, the detection accuracy of the element impedance is decreased. On the other hand, when these signal components are amplified on the basis of the impedance detection signal component, the detection accuracy of the A/F detection signal component is decreased.

In the configuration of the sensor control circuit 20 (as the detection device for detecting an element impedance of the sensor element 10) according to the embodiment, the AC power source circuit 31, the A/F signal output part 41 and the supplying voltage control circuit 21 (excepting the generation part for generating the reference voltage) are integrated on an integrated circuit as a sensor control IC. However, the shunt resistance 33 is formed in the sensor control IC in order to decrease a resistance error of the shunt resistance 33. That is, this configuration of the sensor control circuit 20 according to the embodiment makes it possible to use the shunt resistance with high accuracy, and to increase the detection accuracy of the element current IL.

In the configuration of the sensor control circuit 20 according to the embodiment as the detection device for detecting an element impedance of the sensor element 10, the element impedance Rac is detected at the connection node A on the basis of the divided voltage between the resistance component (as the resistance value R1) of the shunt resistance 33 and the resistance (as the element resistance Rae) of the sensor element 10. The changed value $\Delta VA$ of the voltage at the connection node A, which is alternately changed in response to the supplied AC voltage, can be expressed by the following equation (1):

$$\Delta VA = Rae/(R1+Rac) \times \Delta Vac \qquad (1),$$

where $\Delta Vac$ indicates an amplitude of the AC voltage. The embodiment takes R1 of 200Ω and $\Delta Vac \pm 1$ Volt.

According to the above equation (1), the more the element impedance Rac is increased, the more the value of $\Delta VA$ is increased. For example, when the sensor element 10 is activated and the element impedance has 32Ω (Rac=32Ω), $\Delta VA$ becomes±138 mV ($\Delta VA=\pm138$ mV).

On the other hand, when the sensor element 10 is not activated and the element impedance Rac has 110 (Rac=110Ω), $\Delta VA$ becomes±355 mV ($\Delta VA=\pm355$ mV).

In order to eliminate noise from the impedance detection signal Tout, the CPU 50 limits an updated value of the hold voltage value (as the charged voltage) in the P/H circuit 46 every alternating current period (AC period).

A description will now be given of the function of the CPU 50 which limits the updating value of the hold voltage held in the P/H circuit 46 with reference to FIG. 4.

Figure 4:
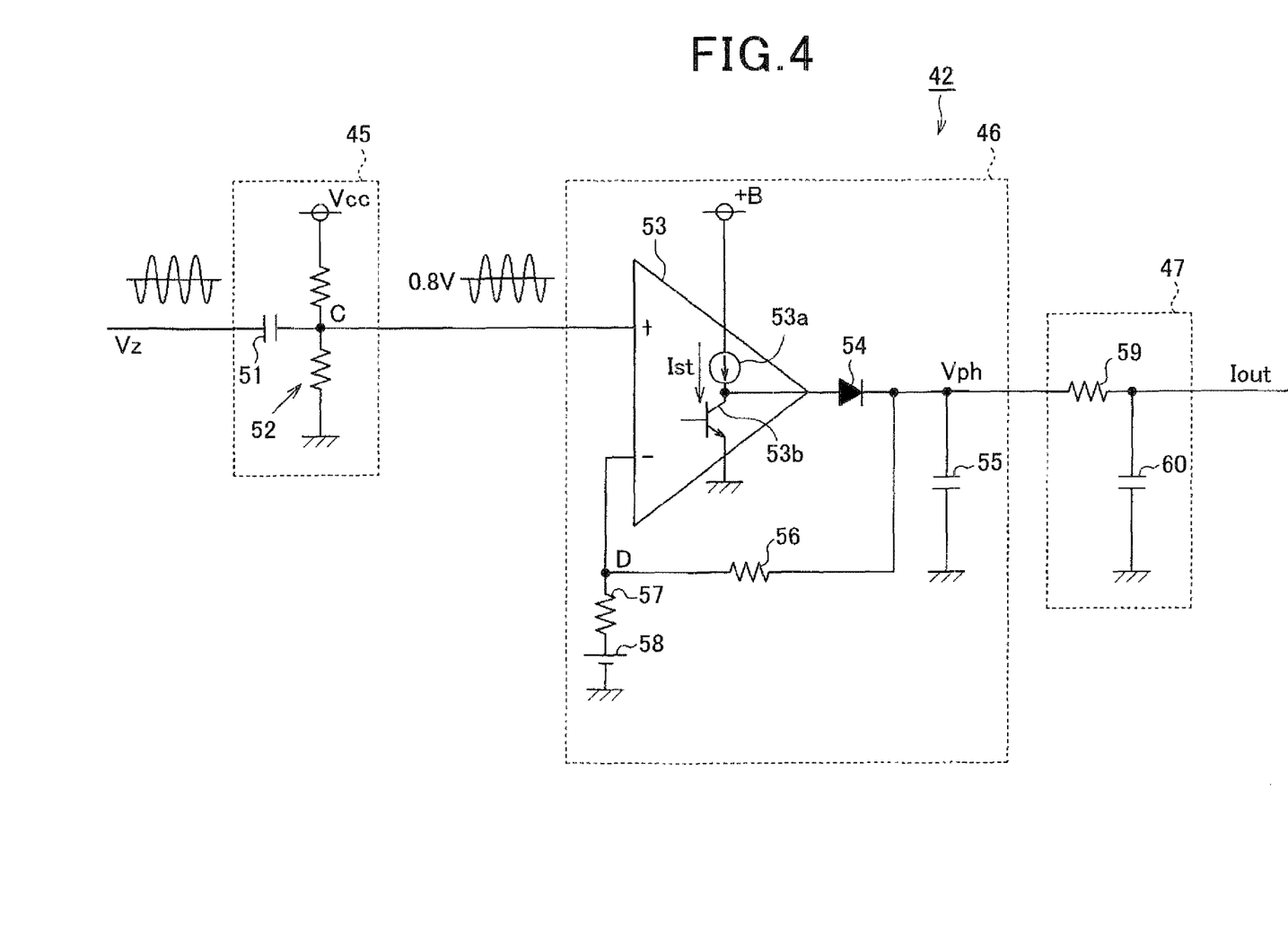
FIG. 4 is a view showing a circuit configuration of an impedance signal output part in the sensor control circuit shown in FIG. 1.

FIG. 4 is a view showing a circuit configuration of the impedance signal output part 42 in the sensor control circuit 20 shown in FIG. 1.

In the configuration shown in FIG. 4, the HPF 45 is comprised of a capacitor 51 and a resistance dividing circuit 52. The resistance dividing circuit 52 is composed of a pair of resistances. The capacitor 51 is connected to the connection node A in order to input the voltage at the connection node A shown in FIG. 1.

The voltage at the connection node A will be referred to the "impedance detection voltage Vz".

The resistance dividing circuit 52 is connected to a constant voltage Vcc (for example, 5 volts). The voltage at the connection node C shown in FIG. 4 is 0.9 volts, for example. The HPF 45 converts the impedance detection voltage Vz to an AC signal whose center voltage is the reference voltage of 0.8 volts, where the impedance detection voltage Vz is the AC current signal having a center voltage with an amplitude of the voltage which corresponds to an A/F at each time.

As shown in FIG. 4, the P/H circuit 46 is comprised of an input comparator 53, a rectifying element 54 and a hold capacitor 55. The input comparator 53 inputs an impedance detection voltage Vz after passing through the HPF 45. The rectifying element 54 is connected to the output terminal of the input comparator 53. The hold capacitor 55 is charged by the output of the input comparator 53. A feedback path is placed to the input comparator 53. The feedback path connects the output terminal to the input terminal of the input comparator 53. A resistance 56 is placed in the way of the feedback path.

As shown in FIG. 4, the connection node D on the negative feedback path of the input comparator 53 is connected to a series circuit. The series circuit is composed of a resistance 57 and a direct current (DC) power source 58. The DC power source 58 supplies the voltage of 0.8 volts to the input comparator 53. This voltage of 0.8 volts is equal to the voltage at the connection node C of the resistance dividing circuit 52. It is controlled for the connection node D to have a voltage of larger than 0.8 volts.

The input comparator 53 adjusts its output so that a voltage at the connection doe D becomes equal to an input voltage of the input terminal (+) of the input comparator 53, where the voltage at the connection node D is determined by a cathode voltage of a diode, a voltage of the DC power source 58 and the resistance value of each of the resistances 56 and 57. The diode forms the rectifying element 54. The input voltage of the input terminal (+) of the input comparator 53 is the hold voltage value Vph held in the hold capacitor 55. That is, the input comparator 53 compares the impedance detection voltage Vz at each time with the current hold value of the hold capacitor 55, and outputs an output signal on the basis of the comparison result.

The input comparator 53 has an internal circuit comprised of a constant current circuit 53a and a transistor 53b. The transistor 53b is a switching element which is turned off when the input voltage (the impedance detection voltage Vz at the connection node C in the HPF 45) at the input terminal (+) of the input comparator 53 exceeds the input voltage (an intermediate value between the hold voltage value Vph and the voltage of 0.8 volts) at the input terminal (−) of the input comparator 53.

That is, when the voltage at the input terminal (+) is greater than the voltage at the input terminal (−), the transistor 53b is turned off and the constant current Its of the constant current circuit 53a flows to the hold capacitor 55 through the rectifying element 54. This current charges the hold capacitor 53b.

On the other hand, when the voltage at the input terminal (+) is less than the voltage at the input terminal (−), the transistor 53b is turned on and the constant current Its of the constant current circuit 53a does not flow into the hold capacitor 55.

The constant current circuit 53a corresponds to the limiting means for limiting the updating value of the hold voltage value Vph every period of time. In particular, when the constant current Ist of the constant current circuit 53a is decreased to a small current in order to limit the output signal of the input comparator 53, this limits the updated value of the hold voltage value Vph. For example, it is preferable for the constant current Ist to have approximately several 100 μA. In the embodiment, the constant current Ist is 450 μA.

When the AC voltage has a frequency of 20 kHz, the time length of one period of time (the time length of one period of the impedance detection voltage Vz) is 50 μsec. The charging voltage capable of charging the hold capacitor 55 during one alternating current (AC) period of time is approximately 50 mV (when the capacitance of the hold capacitor 55 is 0.22 μF). In this case, at the activation state of the sensor element 10 (Rac=32Ω), the changed value $\Delta VA$ of the voltage at the connection node A is 138 mV, it is difficult for the hold capacitor 55, immediately following its reset state (when the hold voltage value Vph is zero volt, Vph=0), to hold the peak value of the impedance detection voltage Vz within one period of time of alternating current (AC). In this case, the hold capacitor 55 can hold the impedance detection voltage Vz within three periods of time of alternating current (AC).

Similarly, during the time before the sensor element 10 is activated, the hold capacitor 55 holds the impedance detection voltage Vz during a plurality of periods. That is, when the changed value ΔVA of the voltage at the connection node A (as the voltage changed value of the impedance detection voltage Vz) in the state (Rac=110Ω) is 355 mV before the sensor element 10 is activated, the hold capacitor 55 holds the peak value of the impedance detection voltage Vz during a time length of eight AC periods of time by the change of the AC voltage at the connection node C.

As described above, when the hold capacitor 55 is reset, the hold voltage value Vth (charging voltage) reaches the peak value of the impedance detection voltage Vz by the alternating current change of the impedance detection voltage Vz. When the hold voltage value Vth reaches the peak value Vz once, the hold capacitor 55 maintains approximately a constant value of the constant hold voltage value Vph unless a large change of impedance detection voltage Vz occurs.

The negative feedback path formed in the input comparator 53 is a discharging path of the hold capacitor 55. The hold capacitor 55 is discharged by the discharging rate which is determined by the total resistance value of the resistances 56 and 57. In this case, the discharging speed of the hold capacitor 55 is lower than the charging speed of the hold capacitor 55. The charging speed of the hold capacitor 55 is determined by the constant current Ist. In the embodiment, the discharging voltage of the alternating current change of the impedance detection voltage Vz per AC period of time is approximately 1.2 mV.

The low pass filter (LPF) 47 is comprised of a resistance 59 and a capacitor 60. The output of the P/H circuit 46 passes through the LPF 47, and is supplied as the impedance detection signal Tout to the CPU 50 as shown in FIG. 1 and FIG. 4.

Figure 5:
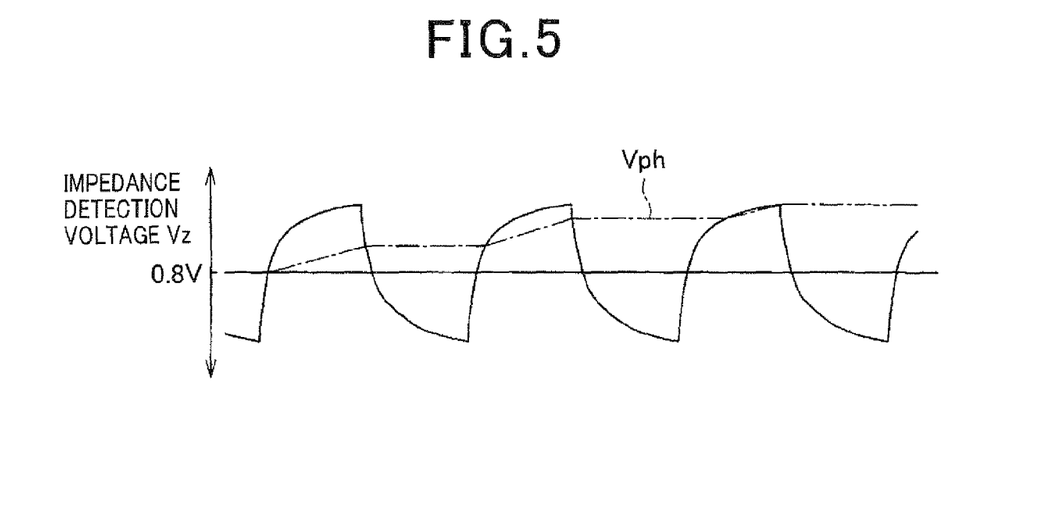
FIG. 5 is a view showing a timing chart of charging of a hold capacitor when the hold capacitor is reset.

FIG. 5 is a view showing a timing chart of charging of the hold capacitor 55 according to the alternating current change (AC change) of the impedance detection voltage Vz when the hold capacitor 55 is reset (the hold voltage value Vph=0). In particular, FIG. 5 shows the signal waveform of the impedance detection voltage Vz when the sensor element 10 is activated.

As shown in FIG. 5, the impedance detection voltage Vz (which corresponds to the voltage at the connection node A shown in FIG. 1) is alternately changed at a predetermined period of time. As shown by the dashed and dotted line in FIG. 5, the hold voltage value Vph is updated in accordance with the AC period of the impedance detection voltage Vz. The impedance detection voltage Vz is the signal after passing through the HPF 45 and alternately changed around 0.8 volts in amplitude.

That is, the hold capacitor 55 is changed according to the positive side in the alternative change of the impedance detection voltage Vz. According to the change of the voltage of the hold capacitor 55, the hold voltage value Vph is increased. In this case, as previously described, because the updated value of the hold voltage value Vph per alternating current period of time is limited, the hold voltage value Vph of the hold capacitor 55 cannot reach the peak value of the impedance detection voltage Vz by the change of the impedance detection voltage Vz per alternating current period of time when the hold capacitor 55 is reset. In the case shown in FIG. 5, the hold voltage value Vph of the hold capacitor 55 can reach the peak value of the impedance detection voltage Vz by the alternative change of the impedance detection voltage Vz before three alternating current (AC) periods of time have elapsed.

Figure 6:
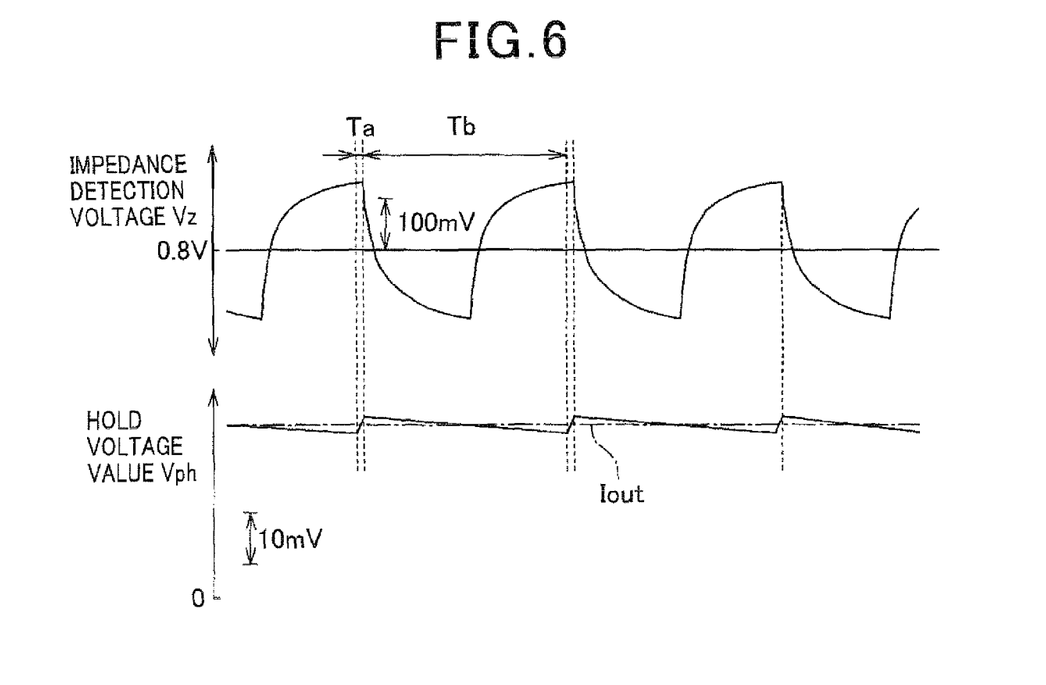
FIG. 6 is a view showing timing charts of various types of signal waveform when the hold voltage value of the hold capacitor reaches a peak value of an impedance detection voltage of the sensor element.

FIG. 6 is a view showing timing charts of various types of signal waveform when the hold voltage value Vph of the hold capacitor 55 reaches the peak value of the impedance detection voltage Vz.

In FIG. 6, the vertical axis in each of the upper timing chart and the bottom timing chart indicates the voltage, and the scale of the vertical axis at the upper timing chart is expanded when compared with the scale of the voltage at the bottom timing chart (this is same of the case shown in FIG. 7 which will be explained later).

In FIG. 6, when the impedance detection voltage Vz is increased at each time, and a new hold voltage value Vph exceeds the current hold voltage value (Vz>Vph), the hold capacitor 55 is changed, and the hold voltage value Vph is increased (for example, see the period Ta).

When the impedance detection voltage Vz which is alternately changed is lower than the current hold value, becomes a value, the capacitance charged in the hold capacitor 55 is discharged through the discharging path (as the negative feedback path) of the input comparator 53, the hold voltage value Vph is thereby decreased (for example, see the period Tb).

The change in increasing and decreasing of the hold voltage value Vph is repeatedly executed according to the alternative change of the impedance detection voltage Vz. This hold voltage value Vph indicates the charged value of the hold capacitor 55. In this case, when there is no change of the element impedance of the sensor element 10, the hold voltage value Vph of the hold capacitor 55 is changed by corresponding to the discharging component in the resistance of the feedback path in the input comparator 53. This change is very small (approximately, 1.2 mV). After the LPF 47 filters the hold voltage value Vph of the hold capacitor 55, an approximate constant voltage is output as the impedance detection signal Tout, designated by the dashed and dotted line in FIG. 6, from the LPF 47 to the CPU 50.

Figure 7:
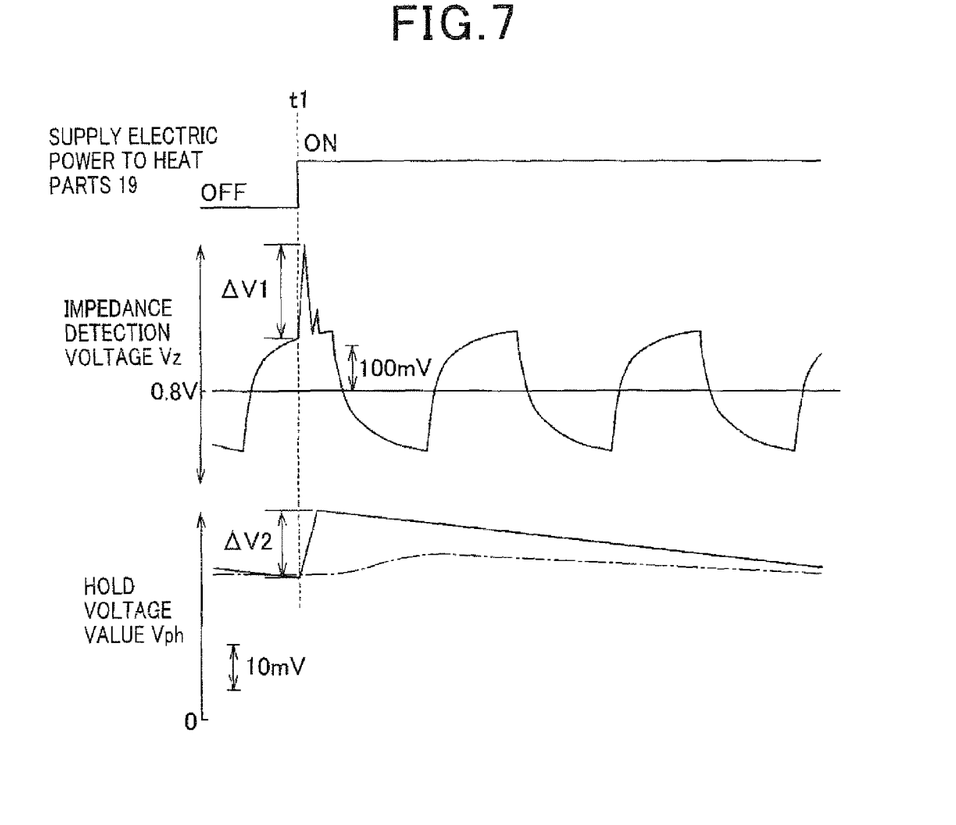
FIG. 7 is a view showing timing charts of various types of signal waveforms when noise is superimposed on the impedance detection voltage Vz when electric power is supplied to heater units in the sensor element.

FIG. 7 is a view showing timing charts of various types of signal waveforms when noise is superimposed on the impedance detection voltage Vz when electric power is supplied to the heater units 19 in the sensor element 10.

As shown in FIG. 7, noise is generated and overlapped or superimposed on the impedance detection voltage Vz when the electric power is supplied to the heater units 19 at timing t1. In this case, during the period in which the impedance detection voltage Vz is temporarily increased by the noise, the impedance detection voltage Vz exceeds the hold voltage value Vph (Vz>Vph), the hold capacitor 55 is charged by the constant current Ist supplied from the constant power source 53a. However, because the updating value of the hold voltage value Vph per period is limited by the constant current Ist, as previously described, the updating value caused by the noise is relatively small, and as a result, the impedance detection signal Iout has a relative small value. Although the actual amplitude of noise (ΔV1) is approximately 140 mV, the change value of the hold voltage value Vph caused by the noise is approximately 10 mV.

The noise generation period has approximately 10 sec. This period is very smaller than the alternating current (AC) period of the impedance detection voltage Vz. This means that the updating period of time of the hold voltage value Vph by the noise is very short. This suppresses the changed value of the hold voltage value Vph caused by the noise.

A description will now be given of the effects of the sensor control circuit 20 as the element impedance detection device according to the embodiment of the present invention.

In order to eliminate the influence of noise from the impedance detection signal Tout, the sensor control circuit 20 has the structure of limiting the updating value of the hold voltage value (charging voltage) in the P/H circuit 46 every alternating current period of time. Accordingly, even if noise is overlapped or superimposed on the impedance detection voltage Vz (impedance response signal), it is possible to limit the changed value of the hold voltage value Vph caused by the noise. This suppresses decreasing of the detection accuracy of the element impedance caused by the noise. In addition, it is possible for the CPU 50 to execute synchronous control at each timing in order to avoid the following two timings from simultaneously occurring: (a) impedance detection timing; and (b) timing for supplying electric power to the heater parts 19 in the sensor element 10.

That is, this can avoid any software which is required for eliminating noise generated when the heater parts 19 are turned on. It is therefore possible for the sensor control circuit 20 as the element impedance detection device according to the embodiment to have a simple software configuration. As a result, it is possible for the sensor control circuit 20 as the element impedance detection device according to the embodiment to enhance the detection accuracy of detecting an element impedance of the sensor element 10 while avoiding influence of noise.

Although ignition noise is generated every ignition in a spark ignition engine and this decreases the detection accuracy of the element impedance of the sensor element 10, it is possible for the sensor control circuit 20 as the element impedance detection device according to the embodiment to detect the element impedance of the sensor element 10 with high accuracy.

In the configuration of the sensor control circuit 20 as the element impedance detection device according to the embodiment of the present invention, the P/H circuit 46 limits the output of the input comparator 53 in order to limit the updating value of hold voltage value Vph of the hold capacitor 55 every alternating current period (AC period) of time. Although the input comparator 53 inputs the impedance detection voltage Vz with noise, the input comparator 53 outputs the impedance detection signal Iout with decreased influence of the noise. It is therefore possible for the sensor control circuit 20 as the element impedance detection device according to the embodiment to eliminate the influence of noise contained in the impedance detection voltage Vz from the impedance detection signal Tout.

The input comparator 53 has the constant current circuit 53*a* which supplies the constant current Ist on the basis of the comparison result of the input values, and the updating value of the hold voltage value Vph is limited on the basis of the constant current Ist. In this case, when the constant current Ist is decreased, the updating value of the hold voltage value Vph is also decreased (the updating speed of the hold voltage value Vph becomes low). On the other hand, when the constant current Ist is increased, the updating value of the hold voltage value Vph is also increased (the updating speed of the hold voltage value Vph becomes high.)

Therefore it is possible for the sensor control circuit 20 as the element impedance detection device according to the embodiment to easily adjust the updating value of the hold voltage value Vph by changing the constant current Ist.

Because the input comparator 53 has the discharging path through the hold capacitor 55 which is discharged at a discharging speed which is lower than the charging speed of the hold capacitor 55 by the constant current Ist, it is possible for the sensor control circuit 20 as the element impedance detection device according to the embodiment to return the hold voltage value Vph to its optimum value after noise is superimposed on the impedance detection voltage Vz.

In addition, when the element impedance of the sensor element 10 is changed by the change of the element temperature, it is possible for the input comparator 53 in the sensor control circuit 20 to decrease and increase the hold voltage value Vph of the hold capacitor 55.

In the configuration of the sensor control circuit 20 as the element impedance detection device according to the embodiment, the impedance detection voltage Vz is detected on the basis of the divided voltage at the connection node A (see FIG. 1) between the sensor element 10 and the shunt resistance 33. Because this divided voltage is obtained by the resistance component (the resistance value R1) of the shunt resistance 33 and the resistance component (the element impedance value Rac), the amplitude of the impedance detection voltage Vz is decreased in accordance with the activation of the sensor element 10 when compared with the amplitude of the impedance detection voltage Vz before the activation of the sensor element 10. Accordingly, it is possible for the sensor control circuit 20 as the element impedance detection device according to the embodiment to decrease the influence of heater noise even if the heater noise is superimposed on the impedance detection voltage Vz.

(Modifications)

A description will now be given of modifications of the sensor control circuit 20 as the element impedance detection device according to the embodiment of the present invention.

Instead of the configuration of the sensor control device 20 previously described, it is possible for the sensor control circuit 20 as the element impedance detection device to have another configuration in which the constant current Ist is supplied to the input comparator 52 in order to limit the updating value of the hold voltage value Vph of the hold capacitor 55. For example, it is possible to place a charging limiting circuit for detecting the increased value of the charged voltage every AC period (which corresponds to an every updating value), and stopping the output of the input comparator 53 when the updating value of the charging voltage reaches a predetermined value.

It is also preferable to place a resistance at the output side of the input comparator 53 in order to limit the charging current which is supplied to the hold capacitor 55.

It is possible for the CPU 50 to have a configuration of changing the period of calculating the element impedance of the sensor element 10. In the configuration of the sensor control circuit 20 as the element impedance detection device according to the embodiment, the AC voltage is always output, and this can detect the element impedance value Rac at every time. For example, during the activation of the sensor element 10 in which a temperature of the sensor element 10 is largely changed, the CPU 50 calculates the element impedance Rac with a short period of time, and during the period after the activation of the sensor element 10 in which the temperature of the sensor element 10 is slowly changed, the CPU 50 calculates the element impedance value Rac at a relatively long period of time.

Although the embodiment previously described omits the configuration of resetting the hold voltage value Vph (charging voltage) of the hold capacitor 55, it is possible for the sensor control circuit 20 as the element impedance detection device according to the embodiment to have a configuration of resetting the hold voltage value Vph.

When the hold voltage value Vph is reset, it is preferable to inhibit the detection of the element impedance of the sensor element 10 on the basis of the hold voltage value Vph during a predetermined period of time after the resetting operation. That is, during the predetermined period of time after the resetting operation, because the voltage hold value Vph reaches the peak value of the impedance detection voltage Vz after a plurality of the periods of the AC voltage change, the sensor control device 20 does not detect the element impedance until at least the hold voltage value Vph reaches the peak value thereof.

In the configuration of the sensor control circuit 20 as the element impedance detection device according to the embodiment, a response current, which is alternately changed in response to the AC voltage supplied to the sensor element 10, is detected as the impedance response signal, and the CPU 50 calculates the element impedance of the sensor element 10 on the basis of the detection result. However, the present invention is not limited by this configuration. For example, it is possible that a response voltage, which is alternately changed in response to the AC voltage which is supplied to the sensor element 10, is detected as the impedance response signal, and the CPU 50 calculates the element impedance of the sensor element 10 on the basis of the detection result.

In the configuration of the sensor control circuit 20 as the element impedance detection device according to the embodiment, the hold capacitor 55 holds the peak value of the impedance response signal (the impedance detection voltage Vz), and the CPU 50 detects the element impedance of the sensor element 10 on the basis of the peak hold value. However, the present invention is not limited by this. For example, it is possible that the hold capacitor 55 holds the impedance detection voltage Vz after a predetermined elapsed of time after the impedance response signal which is alternately changed passes the center of the amplitude thereof, and the CPU 50 detects the element impedance value of the sensor element 10 on the basis of the hold value of the hold capacitor 55.

It is possible to apply the detection device according to the present invention to an A/F sensor equipped with a sensor element whose configuration is different from that of the sensor element 10 shown in FIG. 2. For example, the sensor element has a plurality of cells and each of the cells is made of a solid electrolyte. In more detail, for example, the sensor element has two cells, and each of the cells is made of solid electrolyte. An electromotive force cell is formed on one solid electrolyte, and an oxygen concentration detection cell is formed on the other solid electrolyte. The oxygen concentration detection cell outputs an electric signal which corresponds to the output of the electromotive force cell. This sensor element having the above structure can output two values (for example, 0 V or 0.9 V) which correspond to a lean state and a rich state of fuel mixture. In this case, a supplying voltage to be supplied to the oxygen concentration detection cell is adjusted so that the electromotive force cell outputs a stoichiometry value (e.g. 0.45 V).

In the sensor element having the two cell structure, one of the cells detects the element impedance value of the sensor element. That is, an alternating current signal is supplied to one of the cells (for example, to the electromotive force cell), the CPU detects the element impedance of the sensor element on the basis of the response signal of a current or a voltage which is alternately changed in response to the AC signal while supplying the AC signal. In this case, similar to the embodiment previously described, the hold capacitor (hold means) is provided, which changes its hold value every AC period of the impedance response signal, and the CPU calculates the element impedance of the sensor element on the basis of the hold value of the hold capacitor. In addition, the updating value is limited every AC period when the hold value of the hold capacitor is updated.

It is possible to apply the sensor control circuit 20 as the element impedance detection device according to the present invention to various types of gas sensors capable of detecting a concentration of gas, other than the A/F sensor capable of detecting a concentration of oxygen. For example, a hybrid type gas sensor has a plurality of cells and each of cells is made of solid electrolyte. In the hybrid type gas sensor, a first cell (one pump cell) exhausts and detects a concentration of oxygen contained in a target gas, and a second cell (sensor cell) detects a concentration of gas having a selected component contained in the target detection gas after eliminating oxygen component from the target detection gas. Such a type of the gas sensor is a NOx sensor for detecting a concentration of nitrogen oxide (NOx) contained in exhaust gas emitted from an internal combustion engine such as gasoline engines.

It is possible for such a type of the gas sensor to have a plurality of cells such as a third cell (monitor cell or a second pump cell), in addition to the first cell and the second cell, for detecting a concentration of residual oxygen contained in exhaust gas after eliminating oxygen component from the exhaust gas. Still further, it is possible for such a type of the gas sensor to have a plurality of cell.

It is possible to apply the sensor control circuit 20 as the element impedance detection device according to the present invention to various types of gas sensors for other types of internal combustion engines such as diesel engines. It is also possible to apply the sensor control circuit 20 as the element impedance detection device according to the present invention to other application fields other than motor vehicles. It is also possible for the sensor control circuit 20 as the element impedance detection device according to the embodiment to detect various types of target detection gas other than exhaust gas.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A detection device for detecting an element impedance of a sensor element comprised of a solid electrolyte, comprising:

an alternating current signal supplying section configured to supply an alternating current signal to a sensor element; and an impedance detection section configured to detect an element impedance of the sensor element on the basis of one of a current and a voltage of an impedance response signal which is transmitted from the sensor element and alternately changed in response to the alternating current signal supplied to the sensor element, wherein the impedance detection section comprises:

an input comparator configured to input the impedance response signal and a hold value, to compare the impedance response signal with the hold value, and to output an output voltage on the basis of the comparison result;

a hold capacitor configured to be charged by the output voltage supplied from the input comparator and to hold the hold value on the basis of the charged amount and the hold value in the hold capacitor being sequentially updated every time of an alternately changing period of the impedance response signal; and a limit section configured to adjust the output voltage of the input comparator in order to extend the time to update the hold value of the hold capacitor.

2. The detection device for detecting an element impedance of a sensor element according to claim 1, wherein the input comparator comprises a constant current circuit which serves as the limit section capable of supplying a constant current when the hold capacitor is charged,
   wherein an updating speed of the hold value of the hold capacitor is determined by the constant current supplied from the constant current circuit, and a change of the output voltage of the input comparator is limited by the updating speed.

3. The detection device for detecting an element impedance of a sensor element according to claim 2, wherein the impedance detection section comprises a discharge section configured to discharge the hold capacitor at a discharging speed which is lower than the charging speed of the constant current supplied by the constant current circuit.

4. A sensor unit comprising:
   the detection device for detecting an element impedance of the sensor element according to claim 3; and
   a gas sensor comprising the sensor element and being connected to the detection device for detecting an element impedance of the sensor element.

5. The detection device for detecting an element impedance of a sensor element according to claim 2, wherein the impedance detection section comprises a reset section configured to reset the hold value, and
   the impedance detection section inhibits the detection of the element impedance of the sensor element during a predetermined period counted from the reset of the hold value.

6. A sensor unit comprising:
   the detection device for detecting an element impedance of the sensor element according to claim 2; and
   a gas sensor comprising the sensor element and being connected to the detection device for detecting an element impedance of the sensor element.

7. The detection device for detecting an element impedance of a sensor element according to claim 1, wherein the impedance detection section comprises a reset section configured to reset the hold value, and
   the impedance detection section inhibits the detection of the element impedance of the sensor element during a predetermined period counted from the reset of the hold value.

8. A sensor unit comprising:
   the detection device for detecting an element impedance of the sensor element according to claim 1; and
   a gas sensor comprising the sensor element and being connected to the detection device for detecting an element impedance of the sensor element.

* * * * *